US 011576793B2

(12) United States Patent
Lutz et al.

(10) Patent No.: US 11,576,793 B2
(45) Date of Patent: Feb. 14, 2023

(54) IMPLANTABLE NUCLEAR PROSTHESIS

(71) Applicant: SPINAL STABILIZATION TECHNOLOGIES LLC, San Antonio, TX (US)

(72) Inventors: James D. Lutz, San Antonio, TX (US); W. Loren Francis, Lyons, CO (US); Mark Novotny, Frisco, CO (US)

(73) Assignee: SPINAL STABILIZATION TECHNOLOGIES LLC, San Antonio, TX (US)

( * ) Notice: Subject to any disclaimer, the term of this patent is extended or adjusted under 35 U.S.C. 154(b) by 453 days.

(21) Appl. No.: 16/806,580

(22) Filed: Mar. 2, 2020

(65) Prior Publication Data
US 2020/0229947 A1     Jul. 23, 2020

Related U.S. Application Data

(62) Division of application No. 15/254,282, filed on Sep. 1, 2016, now Pat. No. 10,575,967.

(Continued)

(51) Int. Cl.
*A61F 2/44*     (2006.01)
*A61F 2/46*     (2006.01)
*A61F 2/30*     (2006.01)

(52) U.S. Cl.
CPC ............ *A61F 2/4611* (2013.01); *A61F 2/441* (2013.01); *A61F 2002/30069* (2013.01); *A61F 2002/30462* (2013.01); *A61F 2002/30586* (2013.01); *A61F 2002/30593* (2013.01); *A61F 2002/444* (2013.01); *A61F 2002/4435* (2013.01);

(Continued)

(58) Field of Classification Search
CPC .......... A61F 2/441; A61F 2/442; A61F 2/444
See application file for complete search history.

(56) References Cited

U.S. PATENT DOCUMENTS 3,875,595 A    8/1975  Froning
4,187,390 A    2/1980  Gore
(Continued)

FOREIGN PATENT DOCUMENTS

CA    2468908         6/2003
CN    101076302 A     11/2007
(Continued)

OTHER PUBLICATIONS

First Examination Report from the Indian Patent Office issued in corresponding Application No. 8509/DELNP/2015 dated Oct. 28, 2020.

(Continued)

*Primary Examiner* — Zade Coley
(74) *Attorney, Agent, or Firm* — Norton Rose Fulbright US LLP

(57) ABSTRACT

A nuclear disc implant includes an inner fillable enclosure and an outer fillable enclosure. After insertion into a enucleated disc cavity, the inner enclosure is filled with a fluid and the outer fillable enclosure is filled with a curable material. The curable material is allowed to cure and the fluid is removed from the inner enclosure to leave an inner enclosure surrounded by an cured outer enclosure. A reinforcing band may be provided around the nuclear disc implant. An inflation tool to fill the nuclear disc implant is provided.

20 Claims, 11 Drawing Sheets

Related U.S. Application Data

(60) Provisional application No. 62/212,950, filed on Sep. 1, 2015.

(52) U.S. Cl.
CPC ................ *A61F 2002/4495* (2013.01); *A61F 2002/4635* (2013.01)

(56) References Cited

U.S. PATENT DOCUMENTS

| | | | |
|---|---|---|---|
| 4,478,898 A | 10/1984 | Kato | |
| 4,517,979 A * | 5/1985 | Pecenka | A61B 17/12136 604/97.02 |
| 4,619,641 A | 10/1986 | Schanzer | |
| 4,743,480 A | 5/1988 | Campbell et al. | |
| 5,123,926 A | 6/1992 | Pisharodi | |
| 5,152,782 A | 10/1992 | Kowligi et al. | |
| 5,181,921 A | 1/1993 | Makita et al. | |
| 5,192,310 A | 3/1993 | Herweck et al. | |
| 5,192,326 A | 9/1993 | Bao et al. | |
| 5,437,661 A | 8/1995 | Rieser | |
| 5,439,464 A | 8/1995 | Shapiro | |
| 5,466,509 A | 11/1995 | Kowligi et al. | |
| 5,571,189 A | 5/1996 | Kuslich | |
| 5,628,786 A | 5/1997 | Banas et al. | |
| 5,674,295 A | 7/1997 | Ray et al. | |
| 5,645,597 A | 8/1997 | Krapiva | |
| 5,702,449 A | 12/1997 | McKay | |
| 5,752,969 A | 5/1998 | Cunci et al. | |
| 5,827,327 A | 10/1998 | McHaney et al. | |
| 5,860,425 A | 1/1999 | Benderev et al. | |
| 5,865,845 A | 2/1999 | Thalgott | |
| 5,879,366 A | 3/1999 | Shaw et al. | |
| 5,888,220 A | 3/1999 | Felt | |
| 5,888,226 A | 3/1999 | Rogozinski | |
| 5,890,268 A | 6/1999 | Mullen et al. | |
| 5,910,277 A | 6/1999 | Ishino et al. | |
| 5,928,284 A | 7/1999 | Mehdizadeh | |
| 5,935,147 A | 8/1999 | Kensey et al. | |
| 5,954,767 A | 9/1999 | Pajotin et al. | |
| 5,981,826 A | 9/1999 | Ku et al. | |
| 5,972,022 A | 10/1999 | Huxel | |
| 5,976,174 A | 11/1999 | Ruiz | |
| 5,990,378 A | 11/1999 | Ellis | |
| 6,001,125 A | 12/1999 | Golds et al. | |
| 6,001,130 A | 12/1999 | Bryan et al. | |
| 6,007,570 A | 12/1999 | Sharkey et al. | |
| 6,007,575 A | 12/1999 | Samuels | |
| 6,019,793 A | 2/2000 | Perren et al. | |
| 6,036,724 A | 3/2000 | Lentz et al. | |
| 6,127,597 A | 3/2000 | Beyer et al. | |
| 6,079,868 A | 6/2000 | Rydell | |
| 6,126,682 A | 10/2000 | Sharkey et al. | |
| 6,140,452 A | 10/2000 | Felt et al. | |
| 6,146,419 A | 11/2000 | Eaton | |
| 6,180,848 B1 | 1/2001 | Flament et al. | |
| 6,183,518 B1 | 2/2001 | Ross et al. | |
| 6,206,921 B1 | 3/2001 | Guagliano et al. | |
| 6,224,630 B1 | 5/2001 | Bao et al. | |
| 6,248,131 B1 | 6/2001 | Felt et al. | |
| 6,264,695 B1 | 7/2001 | Stay | |
| 6,332,894 B1 | 12/2001 | Stalcup et al. | |
| 6,344,054 B1 | 2/2002 | Parodi | |
| 6,361,637 B2 | 3/2002 | Martin et al. | |
| 6,375,682 B1 | 4/2002 | Fleischmann et al. | |
| 6,390,992 B1 | 5/2002 | Morris et al. | |
| 6,395,032 B1 | 5/2002 | Gauchet | |
| 6,398,803 B1 | 6/2002 | Layne et al. | |
| 6,402,750 B1 | 6/2002 | Atkinson et al. | |
| 6,419,704 B1 | 7/2002 | Ferree | |
| 6,428,576 B1 | 8/2002 | Haldimann | |
| 6,436,143 B1 | 8/2002 | Ross et al. | |
| 6,443,988 B2 | 9/2002 | Felt et al. | |
| 6,482,234 B1 | 11/2002 | Weber et al. | |
| 6,533,818 B1 | 3/2003 | Weber et al. | |
| 6,527,804 B1 | 4/2003 | Gauchet et al. | |
| 6,582,466 B1 | 6/2003 | Gauchet | |
| 6,596,008 B1 | 7/2003 | Kambin | |
| 6,632,235 B2 * | 10/2003 | Weikel | A61B 17/7258 606/198 |
| 6,645,248 B2 | 11/2003 | Casutt | |
| 6,673,103 B1 | 1/2004 | Golds et al. | |
| 6,689,125 B1 | 2/2004 | Keith et al. | |
| 6,712,853 B2 | 3/2004 | Kuslich | |
| 6,733,533 B1 | 5/2004 | Lozier | |
| 6,780,497 B1 | 8/2004 | Walter | |
| 6,733,532 B1 | 11/2004 | Gauchet et al. | |
| 6,852,223 B2 | 2/2005 | Huang et al. | |
| 6,866,681 B2 | 3/2005 | Laboureau et al. | |
| 6,893,465 B2 | 5/2005 | Huang | |
| 6,893,466 B2 | 5/2005 | Trieu | |
| 6,852,095 B1 | 8/2005 | Ray | |
| 6,932,843 B2 | 8/2005 | Smith et al. | |
| 6,936,070 B1 | 8/2005 | Muhanna | |
| 6,958,077 B2 | 10/2005 | Suddaby | |
| 6,969,404 B2 | 11/2005 | Ferree | |
| 6,969,405 B2 | 11/2005 | Suddaby | |
| 6,984,246 B2 | 1/2006 | Huang | |
| 7,001,431 B2 | 2/2006 | Bao et al. | |
| 7,004,971 B2 | 2/2006 | Serhan et al. | |
| 7,056,345 B2 | 6/2006 | Kuslich | |
| 7,008,427 B2 | 7/2006 | Sevrain | |
| 7,077,865 B2 | 7/2006 | Bao et al. | |
| 7,133,001 B2 | 7/2006 | Mrstik et al. | |
| 7,156,861 B2 | 1/2007 | Scribner et al. | |
| 7,156,877 B2 * | 1/2007 | Lotz | B29C 41/14 623/17.16 |
| 7,182,783 B2 | 2/2007 | Trieu | |
| 7,204,851 B2 | 4/2007 | Trieu et al. | |
| 7,220,282 B2 | 5/2007 | Kuslich | |
| 7,267,687 B2 | 9/2007 | McGuckin et al. | |
| 7,273,497 B2 | 9/2007 | Ferree | |
| 7,201,751 B2 | 10/2007 | Zucherman et al. | |
| 7,201,776 B2 | 10/2007 | Ferree et al. | |
| 7,297,158 B2 | 11/2007 | Jensen | |
| 7,309,359 B2 | 12/2007 | Trieu et al. | |
| 7,556,650 B2 | 7/2009 | Collins et al. | |
| 7,563,284 B2 | 7/2009 | Coppes et al. | |
| 7,618,461 B2 | 11/2009 | Trieu | |
| 7,632,291 B2 | 12/2009 | Stephens et al. | |
| 7,632,294 B2 | 12/2009 | Milbodker et al. | |
| 7,641,691 B2 * | 1/2010 | Lotz | A61F 2/441 623/17.12 |
| 7,645,301 B2 | 1/2010 | Hudgins et al. | |
| 7,713,301 B2 | 5/2010 | Bao et al. | |
| 7,722,612 B2 | 5/2010 | Sala et al. | |
| 7,731,753 B2 | 6/2010 | Reo et al. | |
| 7,766,965 B2 | 8/2010 | Bao et al. | |
| 7,789,913 B2 | 9/2010 | Collins et al. | |
| 7,799,079 B2 | 9/2010 | Hestad et al. | |
| 7,837,733 B2 | 11/2010 | Collins et al. | |
| 7,842,055 B2 | 11/2010 | Pintar et al. | |
| 7,896,920 B2 | 3/2011 | Yuksel et al. | |
| 7,931,689 B2 | 4/2011 | Hochschuler et al. | |
| 7,947,079 B2 | 5/2011 | Helm et al. | |
| 7,972,351 B2 | 5/2011 | Trinidad | |
| 7,993,404 B2 | 8/2011 | Trieu | |
| 7,998,210 B2 | 8/2011 | Edie et al. | |
| 7,993,351 B2 | 9/2011 | Worley et al. | |
| 8,012,210 B2 | 9/2011 | Lin et al. | |
| 8,012,211 B2 | 9/2011 | Kuslich | |
| 8,043,381 B2 | 10/2011 | Hestad et al. | |
| 8,066,758 B2 | 11/2011 | Bogert et al. | |
| 8,083,800 B2 | 12/2011 | Edie | |
| 8,092,536 B2 | 1/2012 | Ahrens et al. | |
| 8,100,978 B2 | 1/2012 | Bass | |
| 8,123,808 B2 | 2/2012 | Dewey et al. | |
| 8,133,250 B2 | 3/2012 | Parsonage et al. | |
| 8,142,456 B2 | 3/2012 | Rosqueta et al. | |
| 8,142,489 B2 | 3/2012 | Doran et al. | |
| 8,236,057 B2 | 8/2012 | Wirtel, III et al. | |
| 8,246,682 B2 | 8/2012 | Slivka et al. | |
| 8,287,595 B2 | 10/2012 | Vresilovic et al. | |

(56) References Cited

U.S. PATENT DOCUMENTS

| | | |
|---|---|---|
| 8,292,961 B2 | 10/2012 | Osman |
| 8,317,864 B2 | 10/2012 | Kim |
| 8,337,556 B2 | 12/2012 | Shaolian et al. |
| 8,337,557 B2 | 12/2012 | Collins et al. |
| 8,349,013 B2 | 1/2013 | Zucherman et al. |
| 8,377,131 B2 | 2/2013 | Lin |
| 8,377,136 B2 | 2/2013 | Simonton |
| 8,377,138 B2 | 2/2013 | Reo et al. |
| 8,382,838 B2 | 2/2013 | Baumgartner et al. |
| 8,398,511 B2 | 3/2013 | Sandusky |
| 8,403,987 B2 | 3/2013 | Reo et al. |
| 8,419,839 B2 | 4/2013 | Shimatani |
| 8,444,694 B2 | 5/2013 | Collins et al. |
| 8,449,660 B2 | 5/2013 | Shimatani et al. |
| 8,454,612 B2 | 6/2013 | Lambrecht et al. |
| 8,460,383 B2 | 6/2013 | Wirtel, III et al. |
| 8,480,718 B2 | 7/2013 | Protopsaltis et al. |
| 8,540,772 B2 | 9/2013 | Osman |
| 8,551,172 B2 | 10/2013 | Park |
| 8,562,634 B2 | 10/2013 | Middleton |
| 8,603,171 B2 | 12/2013 | McClellan, III et al. |
| 8,632,592 B2 | 1/2014 | Barrall |
| 8,636,803 B2* | 1/2014 | Hibri .............. A61F 2/441 623/17.12 |
| 8,663,328 B2 | 3/2014 | Justis et al. |
| 8,690,919 B2 | 4/2014 | Lange et al. |
| 8,727,920 B2 | 5/2014 | Sandusky |
| 8,734,459 B1 | 5/2014 | Alobaid |
| 8,747,475 B2 | 6/2014 | Kuslich |
| 8,808,381 B2 | 8/2014 | Kim et al. |
| 8,888,850 B2 | 11/2014 | Linares |
| 8,894,563 B2 | 11/2014 | Connors et al. |
| 8,945,223 B2 | 2/2015 | Trieu |
| 8,979,931 B2 | 3/2015 | Stad et al. |
| 9,486,323 B1 | 11/2016 | Hibri et al. |
| 2002/0026244 A1 | 2/2002 | Trieu |
| 2002/0068975 A1 | 6/2002 | Teitelbaum et al. |
| 2002/0147497 A1 | 10/2002 | Belef et al. |
| 2002/0151979 A1 | 10/2002 | Lambrecht et al. |
| 2002/0198588 A1 | 12/2002 | Armstrong et al. |
| 2003/0028251 A1 | 2/2003 | Mathews |
| 2003/0040772 A1 | 2/2003 | Hyodoh et al. |
| 2003/0114917 A1 | 6/2003 | Holloway et al. |
| 2003/0153976 A1 | 8/2003 | Cauthen et al. |
| 2003/0199979 A1 | 10/2003 | McGuckin, Jr. |
| 2004/0106999 A1 | 3/2004 | Mathews |
| 2004/0186471 A1 | 9/2004 | Trieu |
| 2004/0220672 A1 | 11/2004 | Shadduck |
| 2004/0230309 A1 | 11/2004 | DiMauro et al. |
| 2005/0004578 A1 | 1/2005 | Lambrecht et al. |
| 2005/0015150 A1 | 1/2005 | Lee |
| 2005/0065609 A1 | 3/2005 | Wardlaw |
| 2005/0090901 A1 | 4/2005 | Studer |
| 2005/0113919 A1 | 5/2005 | Cragg et al. |
| 2005/0119752 A1 | 6/2005 | Williams et al. |
| 2005/0119852 A1 | 6/2005 | Iguchi et al. |
| 2005/0137675 A1 | 6/2005 | Dubson et al. |
| 2005/0197702 A1 | 8/2005 | Coppes et al. |
| 2005/0055099 A1 | 10/2005 | Ku |
| 2005/0251259 A1 | 10/2005 | Suddaby |
| 2005/0278029 A1 | 12/2005 | Trieu |
| 2006/0247780 A1 | 2/2006 | Bert |
| 2006/0047296 A1 | 3/2006 | Embry et al. |
| 2006/0149380 A1* | 7/2006 | Lotz .............. A61F 2/442 623/17.11 |
| 2006/0253132 A1 | 11/2006 | Evans et al. |
| 2006/0265077 A1* | 11/2006 | Zwirkoski ........ A61F 2/4611 623/17.14 |
| 2006/0293749 A1 | 12/2006 | Hudgins et al. |
| 2007/0255406 A1 | 1/2007 | Trieu |
| 2007/0060924 A1 | 3/2007 | Choi |
| 2007/0073402 A1 | 3/2007 | Vresilovic |
| 2007/0093906 A1 | 4/2007 | Hudgins |
| 2007/0135921 A1 | 6/2007 | Park |
| 2007/0150061 A1 | 6/2007 | Trieu |
| 2007/0162135 A1 | 7/2007 | Segal et al. |
| 2007/0168031 A1 | 7/2007 | Hudgins et al. |
| 2007/0168042 A1 | 7/2007 | Hudgins et al. |
| 2007/0173935 A1 | 7/2007 | O'Neil et al. |
| 2007/0173940 A1 | 7/2007 | Hestad et al. |
| 2007/0200271 A1 | 8/2007 | Dave |
| 2007/0213732 A1 | 9/2007 | Khanna et al. |
| 2007/0255285 A1 | 11/2007 | Trieu |
| 2007/0265077 A1 | 11/2007 | Tom et al. |
| 2007/0270953 A1 | 11/2007 | Trieu |
| 2007/0162136 A1 | 12/2007 | O'Neil et al. |
| 2007/0288095 A1 | 12/2007 | Wirtel et al. |
| 2008/0046082 A1 | 2/2008 | Lee |
| 2008/0119943 A1 | 5/2008 | Armstrong et al. |
| 2008/0058932 A1 | 6/2008 | Trieu et al. |
| 2008/0132934 A1* | 6/2008 | Reiley ................ A61F 2/4601 606/191 |
| 2008/0154367 A1 | 6/2008 | Justis et al. |
| 2008/0154368 A1 | 6/2008 | Justis et al. |
| 2008/0154373 A1 | 6/2008 | Protopsaltis et al. |
| 2008/0195210 A1 | 8/2008 | Milijasevic et al. |
| 2008/0288073 A1 | 11/2008 | Renganath et al. |
| 2008/0288074 A1 | 11/2008 | O'Neil et al. |
| 2009/0030399 A1* | 1/2009 | Raiszadeh ............ A61F 2/441 604/151 |
| 2009/0076609 A1 | 3/2009 | Stewart |
| 2009/0076610 A1 | 3/2009 | Afzal |
| 2009/0082870 A1 | 3/2009 | Osman |
| 2009/0105823 A1 | 4/2009 | Williams et al. |
| 2009/0112221 A1 | 4/2009 | Burke et al. |
| 2009/0112323 A1* | 4/2009 | Hestad .................. A61F 2/4611 606/279 |
| 2009/0118833 A1 | 5/2009 | Hudgins et al. |
| 2009/0138053 A1 | 5/2009 | Assell et al. |
| 2009/0163994 A1 | 6/2009 | Quigley et al. |
| 2009/0012618 A1 | 8/2009 | Ahrens et al. |
| 2009/0222093 A1* | 9/2009 | Liu .......... A61F 2/442 623/17.12 |
| 2009/0240341 A1 | 9/2009 | Diwan et al. |
| 2009/0299476 A1 | 12/2009 | Diwan et al. |
| 2010/0030216 A1 | 4/2010 | Arcenio |
| 2010/0145462 A1 | 6/2010 | Ainsworth et al. |
| 2010/0191335 A1 | 7/2010 | Root et al. |
| 2010/0256619 A1 | 7/2010 | Teitelbam et al. |
| 2010/0193999 A1 | 8/2010 | Anneaux et al. |
| 2010/0256766 A1* | 10/2010 | Hibri ................ A61F 2/4611 623/17.16 |
| 2010/0292798 A1 | 11/2010 | Maestretti |
| 2011/0022089 A1 | 1/2011 | Assell et al. |
| 2011/0093076 A1 | 4/2011 | Reo et al. |
| 2011/0190753 A1 | 4/2011 | Forrest |
| 2011/0125158 A1 | 5/2011 | Diwan et al. |
| 2011/0264224 A1 | 10/2011 | Ferree |
| 2011/0196499 A1 | 11/2011 | Boucher et al. |
| 2011/0282418 A1 | 11/2011 | Saunders et al. |
| 2011/0319996 A1 | 12/2011 | Barrall |
| 2012/0277862 A1 | 1/2012 | Tomier et al. |
| 2012/0089227 A1 | 4/2012 | Jarzem |
| 2012/0165941 A1 | 6/2012 | Rabiner et al. |
| 2012/0089229 A1 | 12/2012 | Thramann |
| 2012/0310352 A1 | 12/2012 | DiMauro et al. |
| 2012/0316648 A1 | 12/2012 | Lambrecht et al. |
| 2013/0004586 A1 | 1/2013 | Vachon et al. |
| 2013/0103155 A1 | 4/2013 | Tornier et al. |
| 2013/0131806 A1 | 5/2013 | Carpetner |
| 2013/0297026 A1 | 11/2013 | de Villiers et al. |
| 2013/0304212 A1 | 11/2013 | VonGunten |
| 2014/0052250 A1 | 2/2014 | Wirtel et al. |
| 2014/0094914 A1* | 4/2014 | Hibri ................ A61F 2/4611 623/17.12 |
| 2014/0276832 A1 | 9/2014 | Hibri et al. |
| 2014/0277467 A1 | 9/2014 | Hibri et al. |
| 2014/0288656 A1 | 9/2014 | Kuslich |
| 2015/0057752 A1 | 2/2015 | Hibri et al. |
| 2016/0120653 A1 | 5/2016 | Hibri et al. |

(56) References Cited

U.S. PATENT DOCUMENTS

| | | | |
|---|---|---|---|
| 2016/0120654 | A1 | 5/2016 | Hibri et al. |
| 2017/0056195 | A1 | 3/2017 | Lutz et al. |

FOREIGN PATENT DOCUMENTS

| | | |
|---|---|---|
| CN | 101448471 | 6/2009 |
| CN | 101557779 A | 10/2009 |
| CN | 103099689 | 5/2013 |
| JP | 2005511143 | 4/2005 |
| JP | 2012513243 | 6/2012 |
| KR | 20120040309 | 4/2012 |
| WO | WO 2001/097721 | 12/2001 |
| WO | WO 2003/047472 | 6/2003 |
| WO | WO 2006/060482 | 12/2005 |
| WO | WO 2006/025815 | 3/2006 |
| WO | WO 2006/130796 | 12/2006 |
| WO | WO 2007/087404 | 8/2007 |
| WO | WO 2014/158762 | 10/2014 |
| WO | WO 2016/073587 | 5/2016 |

OTHER PUBLICATIONS

Office Action issued in Chinese Patent Application No. 201580066464. 5, dated Aug. 2, 2018, dated Aug. 22, 2018.
Office Action Issued in Corresponding Brazilian Patent Application No. BR112015023003-2, dated Jan. 22, 2020.
Office Action issued in Corresponding Canadian Application No. 2,906,340, dated Mar. 3, 2020.
Supplementary European Search Report issued in European Application No. 15857214.9, dated Oct. 10, 2017.
Notice of Preliminary Rejection from the Korean Intellectual Property Office in corresponding application No. 10-2015-7028728 dated Sep. 28, 2020.
Search Report from China National Intellectual Property Administration issued in corresponding Patent Application No. 201680058105X dated Apr. 23, 2020.
The First Office Action from the China National Intellectual Property Administration issued in corresponding Patent Application No. 201680058105X dated Apr. 30, 2020.
Examination Report No. 1 from IP Australia issued in corresponding Patent Application No. 2016315964 dated May 23, 2020.
Office Action from the United States Patent and Trademark Office issued in corresponding U.S. Appl. No. 15/958,715 dated Sep. 9, 2020.
Notice of Reasons for Rejection from the Japanese Patent Office issued in corresponding patent Application No. 2018-530671 dated Sep. 2, 2020.
Birkenmaier et al. "Minimally Invasive Endoscopic Spinal Surgery" www.spineuniverse.com/displayarticle.pho/article2016.html [Jun. 15, 2009].
International Search Report dated Jun. 17, 2014 for International Application No. PCT/US2014/019911 filed Mar. 3, 2014.
International Search Report dated Jun. 19, 2014 for International Application No. PCT/US2014/019887 filed Mar. 3, 2014.
International Search Report dated Jun. 25, 2014 for International Application No. PCT/US2014/019957 filed Mar. 3, 2014.
International Search Report and Written Opinion for PCT/US2015/058976 dated Jan. 25, 2016.
International Search Report and Written Opinion for PCT/US2015/059011, dated Feb. 15, 2016.
International Search Report and Written Opinion issued in PCT Application No. PCT/US2016/049816, dated Dec. 8, 2016.
Sharma et al., "Manufacturing of Doubly Curved Tubular Composite Structures: Mapping and Weave Modifications," *Thermoplastic Composite Materials*, 15:209-225 (May 2002).
Supplementary European Search Report issued in European Patent Application No. 16842957.9, dated Jul. 26, 2018.
Viscocliosi et al. "Beyond Total Disc: The Future of Spine Surgery," *Spine Non-Fusion Musculoskeletal Investment Research*, pp. 1-289 (May 2004).
Wu et al., "The direct effect of graft compliance mismatch per se on development of host arterial intimal hyperplasia at the anastomotic interface," *Annals of Vascular Surgery*, 7(2): 156-168, (Mar. 1993).
International Search Report and Written Opinion from the International Searching Authority issued in corresponding International application No. PCT/US2019/049548 dated May 7, 2021.
Non-Final Office Action issued by the United States Patent and Trademark Office in related U.S. Appl. No. 16/560,684 dated Apr. 5, 2021.

\* cited by examiner

IMPLANTABLE NUCLEAR PROSTHESIS

CROSS-REFERENCE TO RELATED APPLICATIONS

This application is a divisional of U.S. patent application Ser. No. 15/254,282, filed Sep. 1, 2016, which claims priority to U.S. Provisional Application No. 62/212,950 filed Sep. 1, 2015, the entire contents of which are specifically incorporated herein by reference without disclaimer.

BACKGROUND

1. Field of the Invention

This application relates generally to methods and devices for replacing an intervertebral disc. More specifically, the application relates to an implantable disc replacement which may be implanted using minimally invasive surgical techniques or percutaneously, and methods for manufacturing such a disc replacement/prosthesis.

2. Description of Related Art

A common medical issue is back pain due to spinal disc injuries caused by trauma, the aging process or other disorders. One method of treatment that has been proposed is to remove the existing nucleus pulposus and replace it with a nuclear prosthesis formed in situ using open surgery or minimally invasive surgical techniques. One proposed method comprises the steps of (i) providing a mold, such as a balloon, to contain a flowable curable material that can cure in situ within the disc space, (ii) providing a conduit to connect the mold cavity to a source of flowable curable material, (iii) delivering the flowable curable material into the mold to fill the cavity, and (iv) permitting the curable material to cure.

The existing techniques for forming a nuclear prosthesis in situ have not achieved convincing clinical acceptance or commercial success. One problem identified by the present inventors is the substantial difference in the modulus of elasticity between the vertebral bony elements, including the vertebral end plates, and the annulus fibrosus on the one hand, and the implanted elements on the other. The high modulus of elasticity of the implanted material is disadvantageous since it does not dampen impacts or sudden increases in intradiscal pressure during extreme bending or torsion, especially during high loading peaks. The large difference in the modulus of elasticity between implanted disc materials and adjacent tissues can also lead to softening of the vertebral end plates and adjacent bone (spongeosus), resulting in subsidence of the nuclear implant. Migration and expulsion of the implant can also occur.

Therefore, there is a need for an improved nuclear implant.

SUMMARY

In accordance with another exemplary embodiment, a kit for implanting a nucleus replacement device comprises a spinal implant device and an inflation stylus. The inner fillable enclosure has a proximal end with a proximal opening and a distal end with a distal opening. The outer fillable enclosure has a proximal end and a distal end, and the proximal and distal ends of the inner and outer fillable enclosures are coupled together so that the outer fillable enclosure encapsulates the inner fillable enclosure. A distal plug seals the distal opening in the distal end of the inner fillable enclosure and a proximal plug seals the proximal opening in the proximal end of the inner fillable enclosure. The proximal plug has a first lumen for providing access to the inner enclosure and a second lumen for providing access to the outer enclosure. The inflation stylus is adapted to mate with the proximal plug, and the inflation stylus comprises a first lumen for delivering fluid to the inner enclosure and a second lumen for delivering fluid to the outer enclosure.

In some embodiments, a reinforcing band surrounds a perimeter of the outer fillable enclosure. The reinforcing band may comprise a textile. A control element may be coupled to a central zone of the annular reinforcement band. At least one pull string may be coupled to an edge of the annular reinforcing band.

In some embodiments, a delivery sheath surrounds the inflation stylus, wherein the delivery sheath is movable from a delivery position to a deployed position. The control element and at least one pull string are positioned between the delivery sheath and the inflation stylus.

According to an exemplary embodiment, a spinal implant device comprises an inner fillable enclosure and an outer fillable enclosure. The inner fillable enclosure has a proximal end with a proximal opening and a distal end with a distal opening. The outer fillable enclosure has a proximal end and a distal end, and the proximal and distal ends of the inner and outer fillable enclosures are coupled together so that the outer fillable enclosure substantially encapsulates the inner fillable enclosure. A distal plug seals the distal opening in the distal end of the inner fillable enclosure and a proximal plug seals the proximal opening in the proximal end of the inner fillable enclosure. A proximal plug seals the proximal opening in the proximal end of the inner fillable enclosure. The proximal plug has a first lumen for providing access to the inner enclosure and a second lumen for providing access to the outer enclosure. In some embodiments, the first lumen for providing access to the inner enclosure remains open after implantation.

In some embodiments, the inner and outer fillable enclosures comprises a unitary piece of material.

In some embodiments, the proximal plug is adapted to receive an inflation stylus comprising first and second lumens for delivering fluid to the inner and outer enclosures, respectively.

In some embodiments, a reinforcing band surrounds a perimeter of the outer fillable enclosure. The reinforcing band may comprise a textile. A control element may be coupled to a central zone of the annular reinforcement band. At least one pull string may be coupled to an edge of the annular reinforcing band.

In some embodiments, the outer enclosure is filled with a curable silicone material.

In accordance with another exemplary embodiment, a method of implanting a prosthetic device into an intervertebral space having a nucleus pulposus surrounded by an annulus fibrosus comprises penetrating the annulus fibrosus; removing the nucleus pulposus to create a enucleated disc cavity; inserting a fillable disc implant device into the enucleated disc cavity, the fillable disc implant device having an inner fillable enclosure forming an inner enclosure and an outer fillable enclosure coupled to the inner fillable enclosure so that the outer fillable enclosure substantially completely surrounds the inner fillable enclosure; inflating the inner fillable enclosure with a fluidic medium; inflating the outer fillable enclosure with a curable medium; allowing the curable medium to cure; removing the fluidic medium from the inner fillable enclosure; and leaving the inner fillable enclosure vented so that fluids may enter and exit the inner fillable enclosure.

In some embodiments, the fluidic medium comprises a substantially incompressible fluid, such as a contrast medium.

In some embodiments, a reinforcing band for reinforcing the perimeter of the fillable disc implant is provided. The reinforcing band is inserted into the enucleated disc cavity and manipulated to create a pocket for receiving the fillable disc implant. The reinforcing band may be manipulated by pulling an inferior edge of the reinforcing band and a superior edge of the reinforcing band to pull the edges toward the interior of the enucleated disc cavity; and activating a control element in a central portion of the reinforcing band to press the annular reinforcing band outward in the central portion toward the annulus fibrosus of the enucleated disc cavity. The inferior and superior edges of the reinforcing band may be pulled by using inferior and superior pull strings disposed at the inferior and superior edges of the reinforcing band. The control element may be activated by using a flexible ribbon to press the annular reinforcing band outward towards the annulus fibrosus. The pull strings and flexible ribbons may be removed after the outer fillable enclosure is filled.

In accordance with yet another embodiment, a reinforcing band for a spinal disc implant comprises a textile band having a superior edge, an inferior edge, and a central zone between the superior and inferior edges. A superior drawstring is disposed at the superior edge of the textile band for tightening the superior edge of the textile band when pulled and an inferior drawstring disposed at the inferior edge of the textile band for tightening the superior edge of the textile band when pulled. A control element is disposed in the central zone for expanding the central zone. The control element may comprise a metal ribbon.

The term "coupled" is defined as connected, although not necessarily directly. The terms "a" and "an" are defined as one or more unless this disclosure explicitly requires otherwise. The terms "substantially," "approximately," and "about" are defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

A device, system, or component of either that is configured in a certain way is configured in at least that way, but it can also be configured in other ways than those specifically described.

Any embodiment of any of the systems and methods can consist of or consist essentially of—rather than comprise/include/contain/have—any of the described elements, features, and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

DETAILED DESCRIPTION

Figure 1:
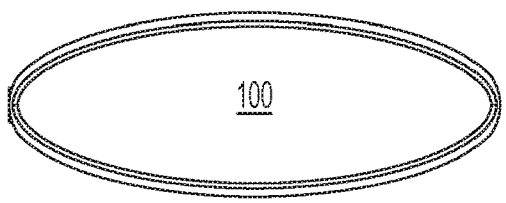
FIG. 1 is a top plan view of an implant in accordance with an embodiment of the present disclosure.
Figure 2:
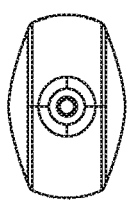
FIG. 2 is a left plan view of the implant of FIG. 1.

In the following detailed description, reference is made to the accompanying drawings, in which are shown exemplary but non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. In the accompanying drawings, like reference numerals refer to like parts throughout the various figures unless otherwise specified.

Nuclear Implant

Referring to FIGS. 1-8, an embodiment of a minimally invasive or percutaneously deliverable spinal implant 100 includes an outer fillable enclosure 102 and an inner fillable enclosure 104. Outer fillable enclosure 102 forms an outer enclosure 106, and inner fillable enclosure 104 forms a inner chamber 108. Inner chamber 108 is encapsulated within outer chamber 102. As used herein, encapsulated means that inner chamber 108 is substantially contained within outer chamber 106 such that inner chamber 108 is substantially surrounded on all sides by outer chamber 106. Outer and inner fillable enclosures 102, 104 may be formed as a seamless, unitary piece of an elastomeric material, such as silicone rubber. The use of an elastomeric material produces compliant outer and inner enclosures 102, 104. That is, the outer and inner enclosures 102, 104 expand as the internal pressure increases when filled with a curable material. The use of compliant enclosures provides certain advantages. Compliant enclosures accommodate the irregular, flat or discoid configuration of the nuclear space. Furthermore, compliant enclosures can help maintain an appropriate modulus of elasticity of the nuclear implant following elastomeric curing, and help preserve bio-mechanical mobility of the vertebral segment, and help allow unhindered deformation of the cured silicone component into the central void. The physical characteristics of inner and outer fillable enclosures 102, 104 may be tailored to provide desired physical outcomes. For example, in some embodiments, enclosures 102, 104 preferentially expand in a transverse plane. In some embodiments, inner and outer fillable enclosures 102, 104 may be completely or partially semi-compliant or non-compliant (i.e., the do not expand or minimally expand as the internal pressure is increased). In some embodiments, different parts of inner and outer fillable enclosures 102, 104 may be formed of different materials to provide different characteristics to enclosures 102, 104.

Implant 100 is preferably sized so that it can be inserted percutaneously or using minimally invasive surgery into a enucleated intervertebral disc cavity while deflated and then filled to fill the enucleated cavity. In one embodiment, the exterior of filled implant 100 is approximately 30 mm in length, 20 mm in width, and 10 mm in height, and the exterior of inner fillable enclosure 104 is approximately 9 mm long, 6 mm wide, and 6 mm thick. In some embodiments, the enclosure does not expand significantly when it is filled (i.e., it is non-compliant or semi-compliant). In other embodiments, the implant is filled so that the implant expands by approximately 100% (i.e., doubles in size) when implanted. In other embodiments, the implant is filled so that the implant expands by more than 100% when implanted.

Outer fillable enclosure 102 has a first (or proximal) end 110 and a second (or distal) end 112. Inner fillable enclosure 104 has a first (or proximal) end 114 coupled to a proximal neck 116. A second (or distal) end 118 of inner fillable enclosure 104 is coupled to a distal neck 120. An end portion 122 of distal neck portion 120 is coupled to distal end 112 of outer fillable enclosure 102, and an end portion 124 of proximal neck 116 is coupled to proximal end 110 of outer fillable enclosure 102. In the illustrated embodiment, end portion 124 of proximal neck 124 is coupled to proximal end 110 of outer fillable enclosure 102 by forming them together as a unitary piece, as will be described in more detail below. Distal end 112 of outer fillable enclosure 102 is inverted and bonded to end portion 122 of distal neck portion to form a substantially fluid tight seal. Coupling the enclosures together in this manner forms a substantially fluid tight outer chamber 106.

A proximal plug 126 is located in the opening formed by proximal neck 116. Proximal neck 116 may have features, such as grooves 148, for mating with matching features on proximal plug 126 to assist in locating proximal plug 126. Proximal plug 126 may be inserted into and bonded with proximal neck 116. Proximal plug 126 is adapted to mate with an inflation tip 192 of an inflation stylus 130. A receptacle 132 receives a first lumen 186 of inflation tip 192 to deliver material through aperture 134 into outer chamber 106. Aperture 134 may be a bottleneck in delivering material to outer chamber 106, and may be formed as a skived hole to maximum the size of aperture 134. Proximal plug 126 may be made of silicone or another material which is compatible with enclosures 102, 104, and may be manufactured using conventional manufacturing techniques, such as injection molding.

In some embodiments, a locking feature to help prevent inadvertent dislodgment of inflation stylus 130 from proximal plug 126 is provided. For example, a recess 136 may be provided in proximal plug 126 and a mating feature (e.g., bead 152, FIG. 13) may be provided on inflation tip 192.

Figure 3:
FIG. 3 is a right plan view of the implant of FIG. 1.
Figure 4:
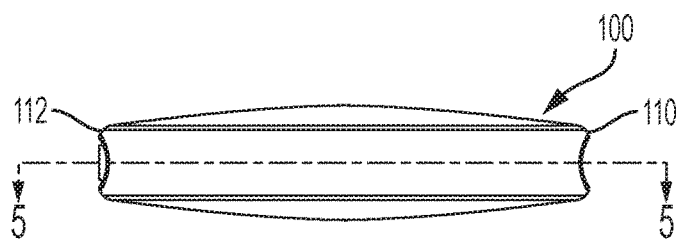
FIG. 4 is a side plan view of the implant of FIG. 1.
Figure 5:
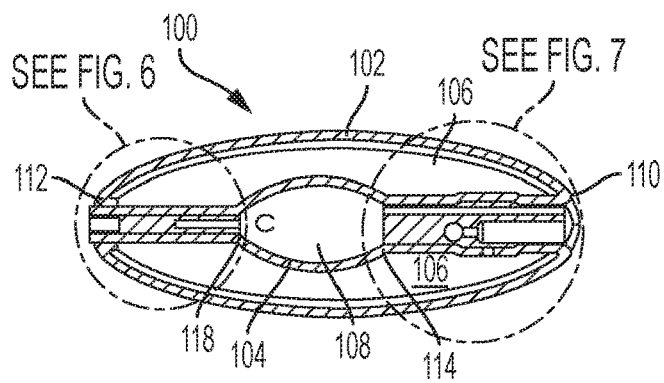
FIG. 5 is a sectional view taken along line 5-5 in FIG. 4.
Figure 6:
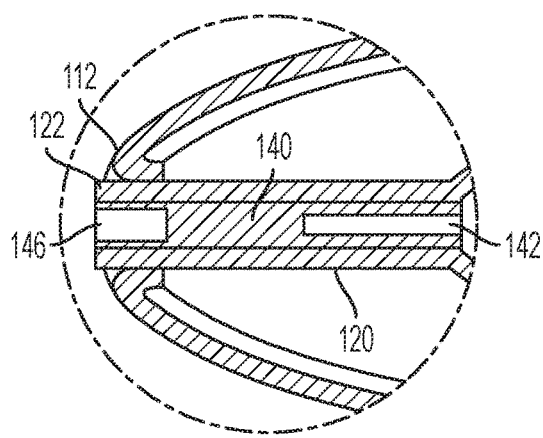
FIG. 6 is an enlarged view of a distal plug of the implant of FIG. 1.
Figure 7:
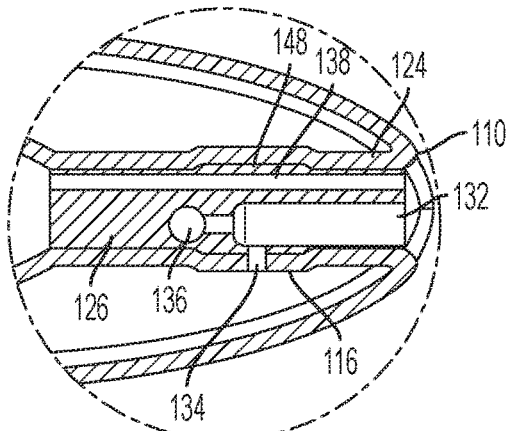
FIG. 7 is an enlarged view of a proximal plug of the implant of FIG. 1.
Figure 10:
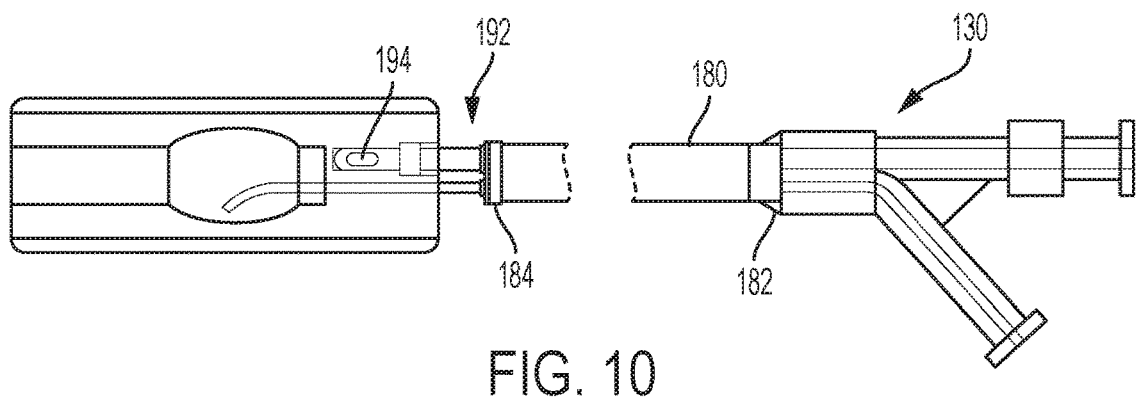
FIG. 10 is an inflation stylus inserted into the distal plug of the implant of FIG. 1.
Figure 11:
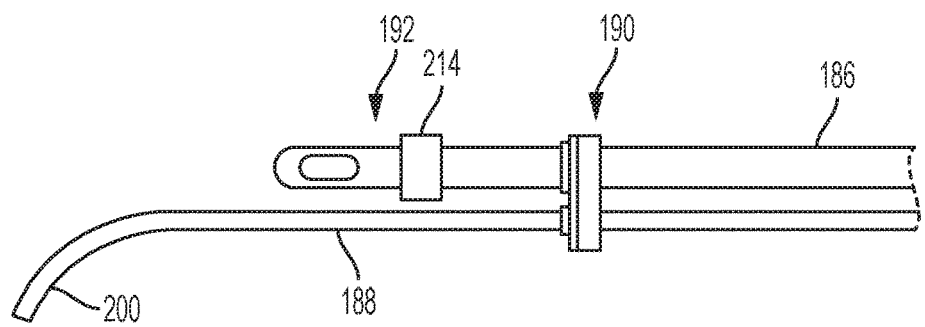
FIG. 11 is a plan view of the distal end of the inflation stylus of FIG. 10.
Figure 12:
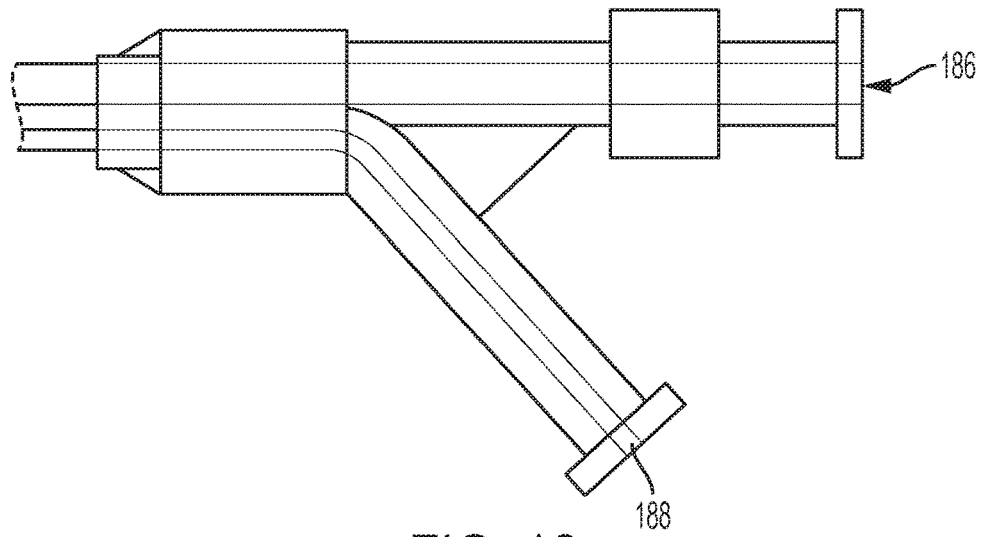
FIG. 12 is a plan view of the proximal end of the inflation stylus of FIG. 10.

An access lumen 138 extends through proximal plug 126 to provide access to interior chamber 108. As can be seen in FIG. 3, receptacle 132 and access lumen 138 can be arranged to prevent improper installation of inflation stylus 130. In some embodiments (such as shown in FIG. 10), a key 214 is provided to physically prevent improper installation of inflation stylus 130. Key 214 may be used to control the depth of insertion of inflation tip 130. Alternatively, in other embodiments, positioning collar 190 may be used to control the depth of insertion of inflation tip 130. Access lumen 138 is configured to remain open after implantation to serve as a vent for internal chamber 108.

A distal plug 140 is disposed in distal neck 120 to seal the distal neck. Distal plug 140 may have a cylindrical recess 142 on the interior side for receiving a distal end 200 of a contrast lumen 188 of inflation stylus 130. Another cylindrical recess 146 may be provided on distal plug 140. Distal plug 140 may be made of silicone or another material which is compatible with enclosures 102, 104, and may be manufactured using conventional manufacturing techniques, such as injection molding.

Textile Band

Referring to FIGS. 14-17, an optional annular reinforcing band 160 may be provided to reinforce implant 100. Annular reinforcing band 160 is useful when a patient's annulus fibrosus is damaged. In one embodiment, annular reinforcing band 160 comprises a tubular, woven textile material. Annular reinforcing band 160 is disposed around the perimeter of the lateral edges of implant 100 to minimize or prevent over inflation of the outer and inner balloons 102, 104 circumferentially. Controlling circumferential expansion also encourages vertical expansion of balloons 102, 104 to distract the adjacent vertebra and widen the disc space. The vertebral superior and inferior end plates constrain the vertical expansion of the implant 100. In some embodiments, annular reinforcing band 160 is formed of a woven material. In one embodiment, annular reinforcing band 160 uses an axial weave which minimizes or substantially prevents shortening of the band when it is expanded. U.S. Pat. No. 8,636,803, entitled Percutaneous Implantable Nuclear Implant, discloses other suitable constructions of annular reinforcing band 160, and is hereby incorporated by reference in its entirety for all purposes. One suitable material for annular reinforcing brand 160 is ultra-high molecular weight polyethylene fiber, such as DYNEEMA® fiber available from Koninklijke DSM N.V., Heerleen, the Netherlands.

Annular reinforcement band 160 has a superior edge 162, an inferior edge 164, and a central zone 166 between superior and inferior edges 162, 164. One or more pull strings and control elements are provided to help place annular reinforcement band during deployment of implant 100. In one embodiment, an inferior pull string 168, a superior pull string 170, and a control element 172 are provided. Superior pull string is placed in a pocket 176 or otherwise coupled to superior edge 162 of annular reinforcement band 160. Similarly, inferior pull string 168 is placed in a pocket 176 or otherwise coupled to inferior edge 164 of annular reinforcement band 160. Inferior and superior pull strings can be used as a drawstring (i.e., pulled) during deployment to pull the edges of annular reinforcement band 160 inward, thereby helping to constrain and position implant 100. Control element 172 is disposed in central zone 166 of annular band 160. If annular band 160 comprises a tubular material, then control element 172 is placed inside the tubular material. In other embodiments, control element 172 is placed in a pocket formed on annular reinforcing band 160. Control element 172 may be a wire, such as a flat ribbon of nitinol, which runs around the perimeter of annular reinforcement band 160. Control element 172 may be used to press annular reinforcement band 160 outward to an annulus fibrosus. Further details of the operation of control element 172 and pull strings 168, 170 will be discussed below.

Inflation Stylus and Delivery Sheath

Referring to FIGS. 10-13, inflation stylus 130 may be used in conjunction with a delivery sheath to deliver implant 100 and annular reinforcement band 160. Inflation stylus 130 comprises a shaft 180 with a proximal end 182 and a distal end 184. A first lumen 186 and a second lumen 188 extend through shaft 180. A positioning collar 190 is provided to maintain first and second lumen 186, 188 in a desired potion. The distal ends of first and second lumens 186, 188 form an inflation tip 192 which is configured to mate with proximal plug 126.

First (or silicone) lumen 186 extends from proximal end 182 of inflation stylus 130 to distal end 184 of inflation stylus 130. When inflation stylus 130 is mated with proximal plug 126, an aperture 194 at the distal end of first lumen 186 is coincident with aperture 134 of proximal plug 126 to allow fluid communication between outer chamber 106 and first lumen 186. Proximal end of lumen 186 is provided with a connector 196 for connection to common inflation tools (such as syringes) known to those of skill in the art.

Figure 13:
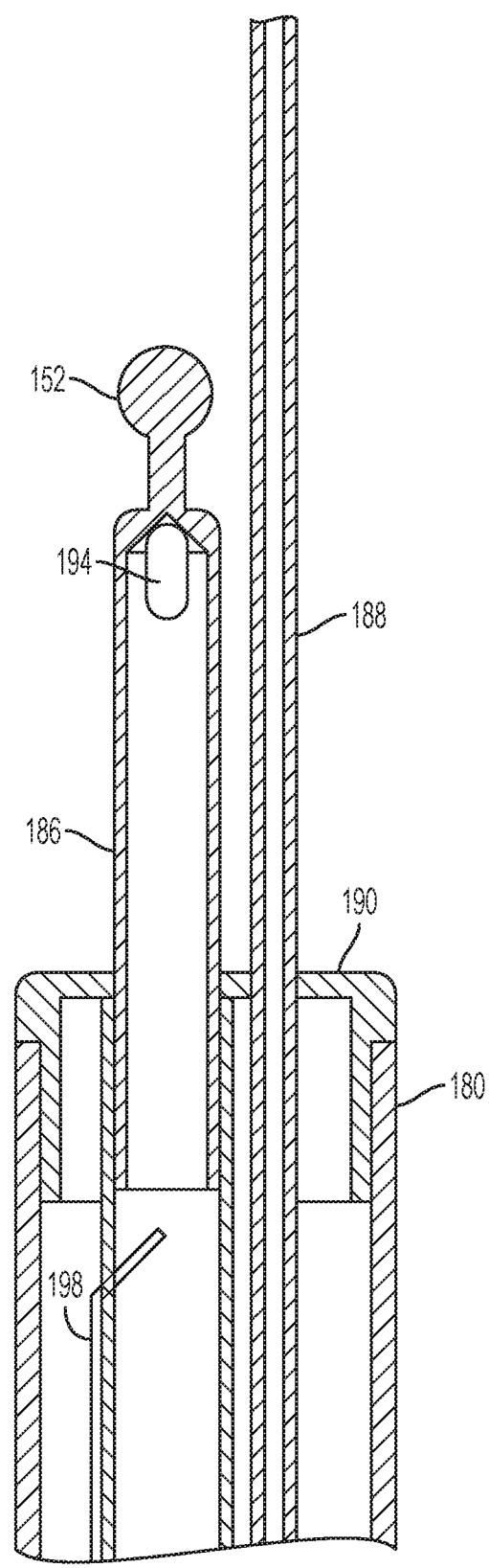
FIG. 13 is a sectional view of the distal end of another inflation stylus.
Figure 14:
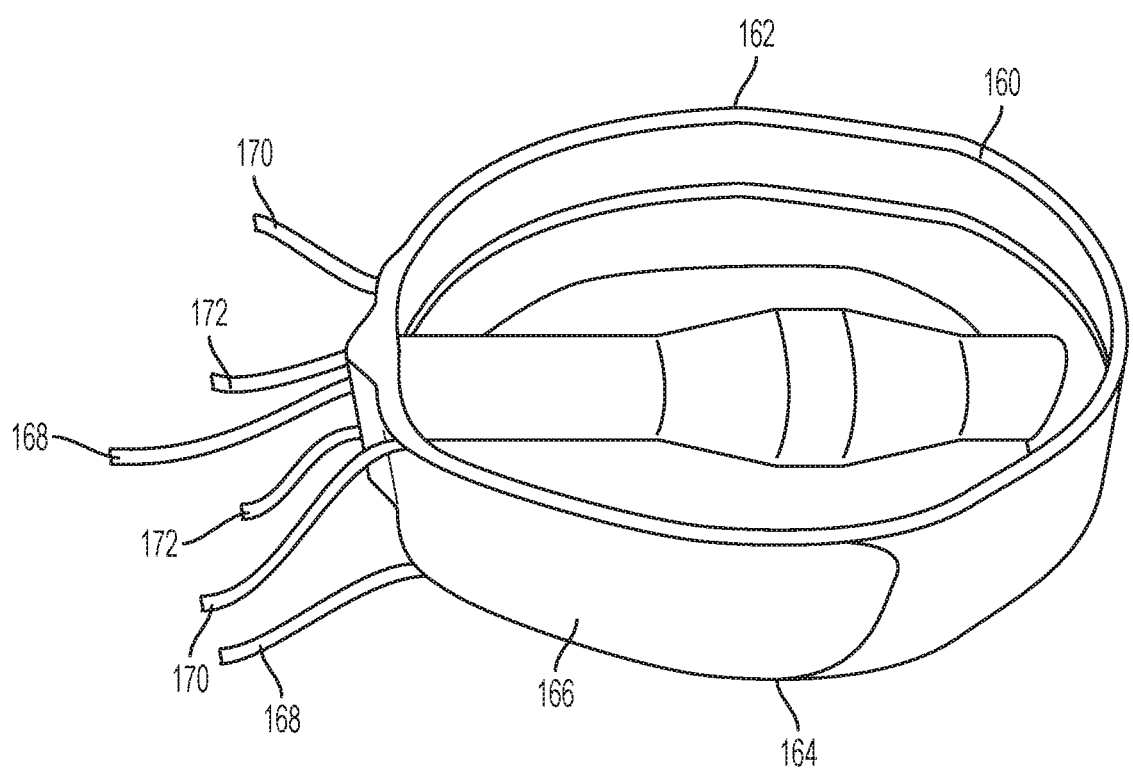
FIG. 14 illustrates an annular reinforcing band for use with the implant of FIG. 1, with a deflated implant located in the interior of the band.
Figure 15:
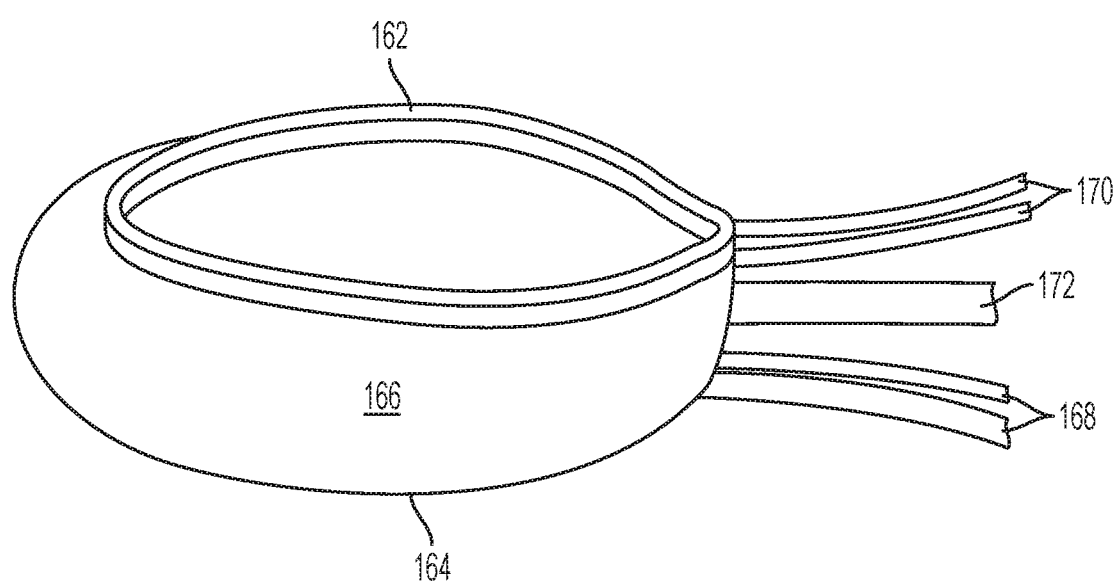
FIG. 15 illustrates the annular reinforcing band of FIG. 14, with a filled implant.

In certain embodiments, such as that illustrated in FIG. 13, a vent 198 may be provided to allow air to exit silicone lumen 186 when silicone or another suitable material is delivered to outer chamber 106. Vent 198 may be large enough to allow air to freely move through it, while resisting more viscous fluids such as curable silicone. It should be understood that as used herein, "silicone lumen" means a lumen for delivery of any desired fluid to outer chamber 106, and can encompass materials other than silicone. Vent 198 preferably extends through shaft 180 to vent to atmosphere at the proximal end of inflation stylus 130.

Second (or contrast) lumen 188 extends from proximal end 182 of inflation stylus 130 to distal end 184 of inflation stylus 130. Contrast lumen 188 extends out the proximal end of inflation stylus 130. Preferably, contrast lumen 188 is independently movable with respect to inflation stylus 130 so that the position of the distal end 200 of contrast lumen 188 may be extended and withdrawn with respect to the distal end 184 of inflation stylus 130. For delivery prior to implantation, contrast lumen 188 can extend through access lumen 138 and the distal tip of contrast lumen 188 can be positioned within recess 142 of distal plug 140 to hold it into place. Contrast lumen 188 can be used to both deliver and remove fluids from inner chamber 108. In some embodiments, distal end 200 of contrast lumen 188 is preformed into a shape which allows easier removal of fluid from inner chamber 108. In one specific embodiment, contrast lumen 188 is preformed into a curved shape which allows easier access to the bottom of inner chamber 108. The curved shape combined with the ability to extend and withdraw contrast lumen 188 allows it to be adjusted when used to withdraw fluid from inner chamber 108. It should be understood that as used herein, "contrast lumen" should be understood to mean a lumen for delivery of any desired fluid to inner chamber 108, and can encompass materials other than contrast medium. Contrast medium may be used to ensure visibility under imaging, such as fluoroscopy.

Figure 16:
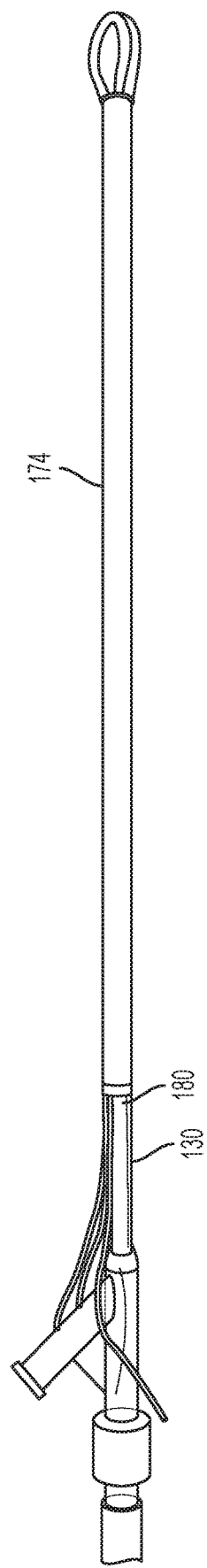
FIG. 16 illustrates the annular reinforcing band of FIG. 14 during deployment.
Figure 17:
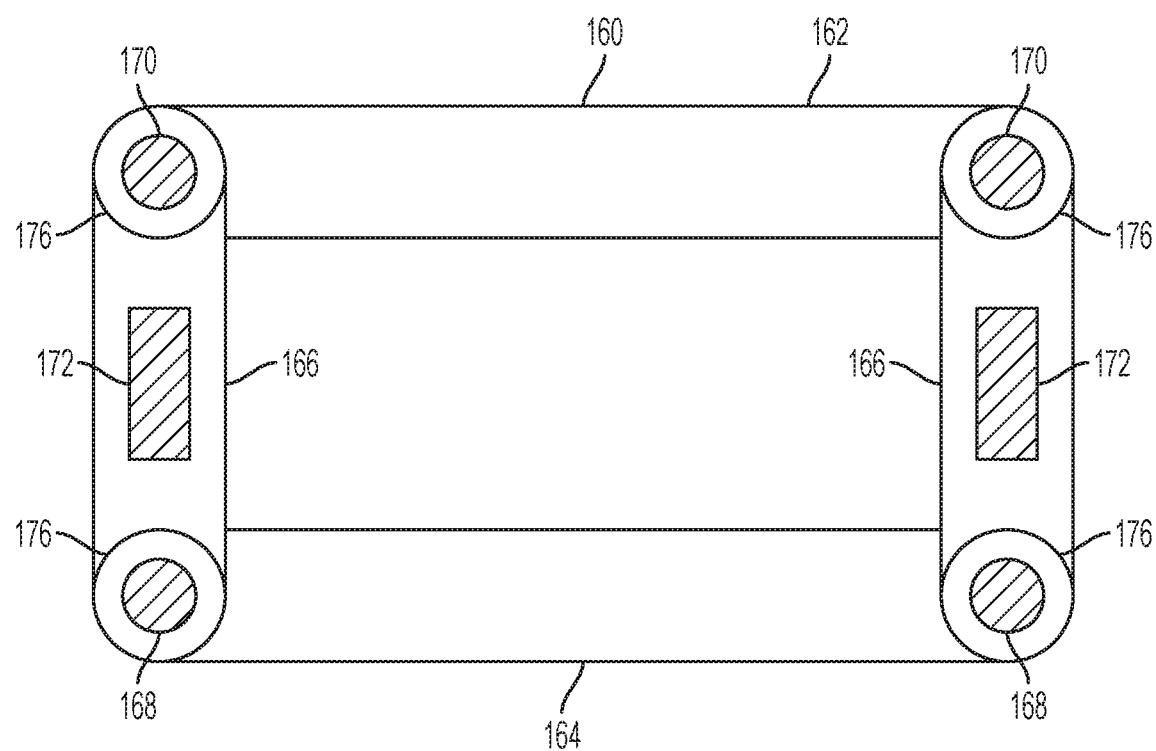
FIG. 17 is a sectional view of the textile band of FIG. 13.

Referring to FIG. 16, a delivery sheath 174 comprises a lumen sized to fit over shaft 180 of inflation stylus 130. To deliver implant 100, implant 100 is placed onto inflation tip 192, and the assembled bodies are withdrawn into the distal end of delivery sheath 174. If pull wires 168, 170 and control element 172 are used, they may be placed through the lumen of the delivery sheath.

Method of Manufacturing an Implant

Figure 8:
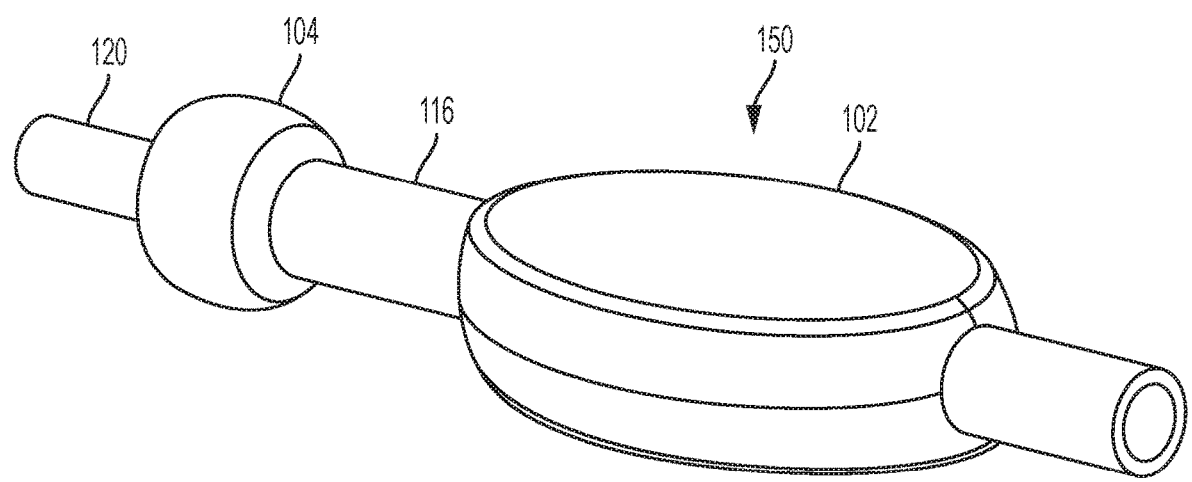
FIG. 8 is a perspective view of an implant blank for forming the implant of FIG. 1.
Figure 9:
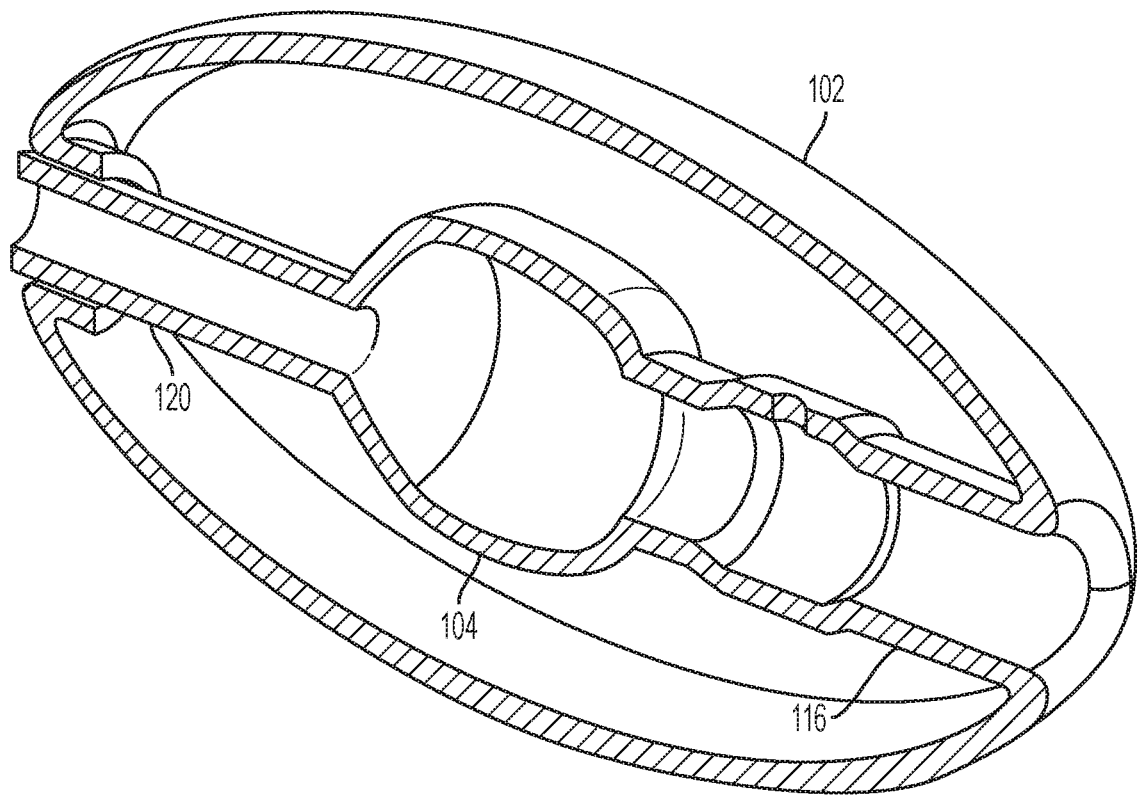
FIG. 9 is a cut-away perspective view of the implant blank of FIG. 8 after the implant blank has been partially inverted.

Referring to FIGS. 8-9, implant 100 may be formed by forming an implant blank 150, which comprises outer fillable enclosure 102 coupled to inner fillable enclosure 104. Implant blank 150 may be manufactured using conventional manufacturing techniques, such as injection molding or dip molding. After implant blank 150 is formed, implant blank 150 is partially inverted to place inner fillable enclosure 104 into the interior of outer fillable enclosure 102. Distal plug 140 is inserted into distal neck 120, and proximal plug 126 is inserted into proximal neck 116. Additional details regarding one suitable manufacturing technique are disclosed in co-pending application 62/074,295, entitled "Percutaneous Implantable Nuclear Prosthesis," which was filed on Nov. 4, 2014 and is hereby incorporated by reference in its entirety.

Method of Deploying an Implant

Referring to FIGS. 18-23, fillable implant 100 is particularly well suited for deployment using minimally invasive or percutaneous surgical techniques.

To implant fillable implant 100, the existing nucleus pulposus is removed by performing a discectomy while leaving annulus fibrosus 202 substantially intact. Preferably, the discectomy is performed using minimally invasive surgical techniques, such as percutaneous techniques, which uses a cannula 208 to access the disc cavity 206 through a small opening in annulus fibrosus 202. In one embodiment, the disc cavity is accessed using a posterolateral approach through Kambin's triangle. An anterior approach may also be used. To preserve the integrity of the annulus fibrosus as much as possible, the annulotomy in the annulus fibrosus may be created by penetrating the fibrosus annulus with a guide pin (e.g., a K-wire) and a series of increasing diameter dilators placed over the guide pin. Once the desired diameter is obtained, the access cannula 208 is placed over the largest diameter, and the dilator set is removed. This procedure spreads the fibrous bands of the annulus fibrosus to create an annulotomy without excising (i.e., removing) any tissue, which aids in the healing process. Alternatively, the fibrosus may be stabbed with a scalpel to create vertical slit to gain access to the nucleus space.

Once cannula 208 is in place, the physician may remove the existing disc using any suitable instruments (such as rongeurs). The physician should avoid violating the circumferential annulus or penetrating the superior and inferior vertebral end plates. The physician may monitor the progress of the discectomy by inserting a compliant imaging balloon into the disc space and inflating the imaging balloon with a contrast agent. In some embodiments the imaging balloon comprises a modified implant comprising outer inflatable enclosure 102 without an inner inflatable enclosure. The imaging balloon also serves as a trial implant to predict the volume, shape and placement of the final implant.

Figure 18:
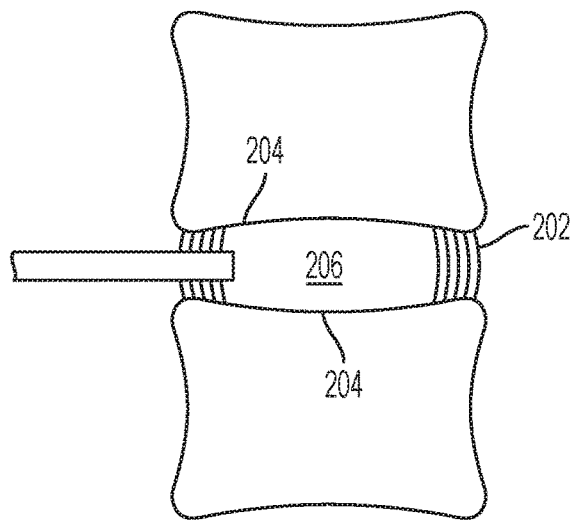
FIG. 18 illustrates a first step in implanting the implant assembly of FIG. 1.
Figure 19:
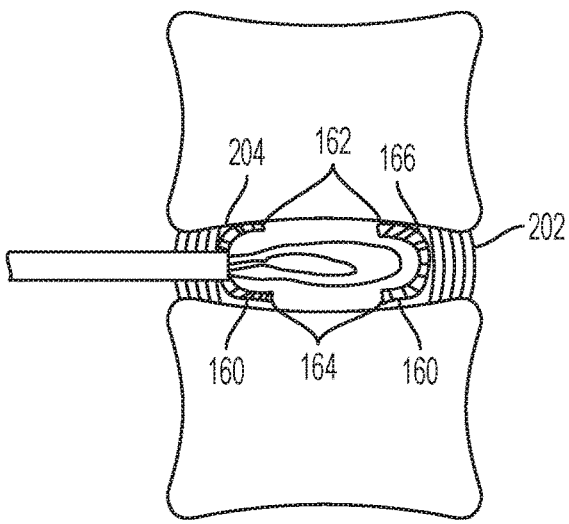
FIG. 19 illustrates a second step in implanting the implant assembly of FIG. 1.
Figure 20:
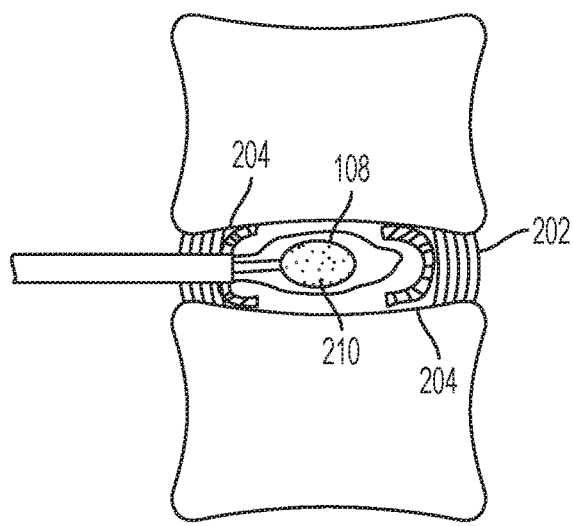
FIG. 20 illustrates a third step in implanting the implant assembly of FIG. 1.
Figure 21:
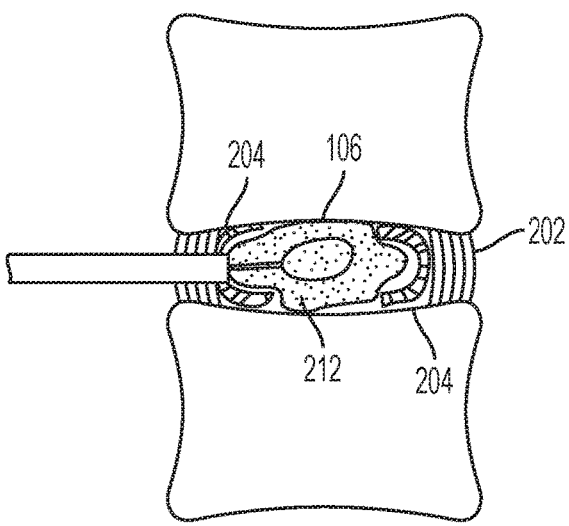
FIG. 21 illustrates a fourth step in implanting the implant assembly of FIG. 1.
Figure 22:
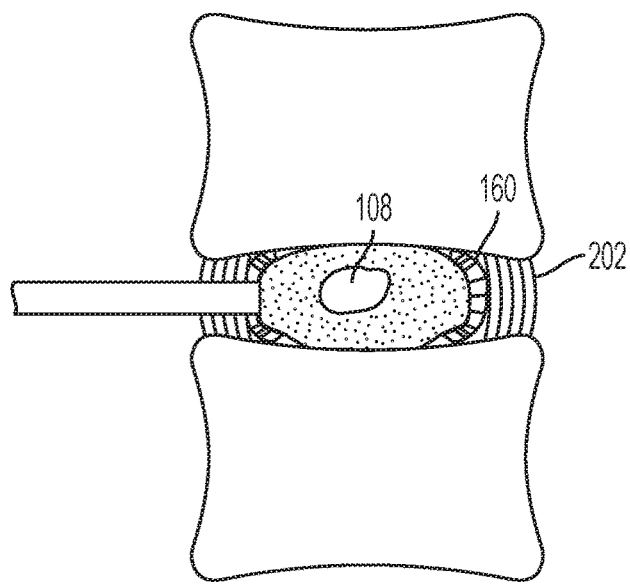
FIG. 22 illustrates a fifth step in implanting the implant assembly of FIG. 1.
Figure 23:
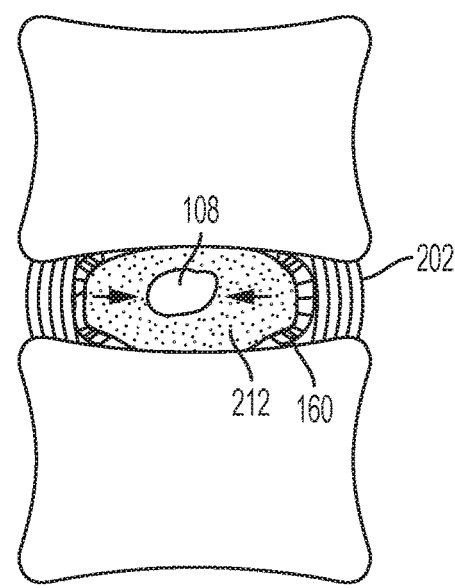
FIG. 23 illustrates a sixth step in implanting the implant assembly of FIG. 1.

Once the existing nucleus pulposus has been removed to the satisfaction of the physician, annulus fibrosus 202 and vertebral end plates 204 form a substantially empty enucleated disc cavity 206 (FIG. 18).

The implant 100, which is loaded into a delivery sheath 174, is placed into enucleated disc cavity 206 through cannula 208. Typically, the implant will be delivered to the far end of the disc cavity. The delivery sheath 174 is then withdrawn to expose the implant 100 inside the enucleated disc cavity.

If the optional annular reinforcing band is provided, control member 172 is manipulated to press central zone 166 of annular reinforcing band 160 substantially flush against the inner surface of annulus fibrosus 202. Pull strings 168, 170 may be pulled to tighten edges 162, 164 of annular reinforcing band 160 and form a pocket for receiving implant 100. Control member 172 and pull strings 168, 170 may include radiopaque features (such as platinum or nitinol coating) to aid in visualization under fluoroscopy.

In some embodiments, inner chamber 108 is first filled with a fluid to a desired size. In one specific embodiment, a substantially incompressible fluid 210 is used, such as a contrast medium. Prior to inflating the inner chamber, air should be purged from the system using, for example, a vacuum locking syringe. Fluid 210 is delivered using contrast lumen 188 of inflation stylus 130. The inflation pressure of the inner chamber 108 is selected to fill inner fillable enclosure 104 to a desired size.

Inflation stylus 130 is used to deliver a curable material 212 to outer chamber 106. Curable material 212 is preferably an elastomeric material, such as silicone rubber containing a radiopaque material (such as barium sulfate). It is not necessary to evacuate air from the outer chamber prior to inflation because of the included vent. Curable material 212 may be chosen so that it polymerizes with the material of inner and outer fillable enclosures 102, 104 to form a unitary member. The modulus of elasticity and other characteristics of curable material 212 can be selected based upon patient specific parameters. For instance, younger, more active patients may require a firmer material than less mobile geriatric patients. Once outer chamber 106 is filled to a desired pressure, curable material 212 is allowed to cure. In some embodiments, the curable material comprises curable silicone which cures in a short period of time, for example, less than 10 minutes, or less than 5 minutes. The use of shorter curing periods may help prevent the dissolution of solvent from the curable medium to the fillable enclosures which may occur with longer curing mediums. Such leaching of solvents may adversely affect the structural integrity of the fillable enclosures.

After curable material 212 is allowed to cure, substantially incompressible fluid 210 is removed using contrast lumen 188. As discussed earlier, contrast lumen 188 may be moved and manipulated to remove as much incompressible fluid 210 as is desired. Preferably, substantially all of fluid 210 is removed; however, some fluid is likely to remain and it is not necessary to remove all fluid.

Once fluid 210 has been removed and curable material 212 is sufficiently cured, inflation stylus 130 can all be withdrawn through cannula 208, and cannula 208 can be removed. If the optional annular reinforcing band is used, pull strings 168, 170, control member 172 are also withdrawn through cannula 208.

Thus, the implant 100 comprises an annular ring of cured material 212 surrounding hollow interior chamber 108. Interior chamber 108 remains open to allow fluids to enter and exit, thereby functioning as a shock absorber. This structure allows for vertical and horizontal load stresses placed on the intervertebral disc space to be redirected inward, centrally toward interior chamber 108 (see direction arrows of FIG. 23) instead of outward. Moreover, annular reinforcing band 160 encourages tissue in-growth of native annulus fibrosus 202, thereby providing reinforcement to native annulus fibrosus 202.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted (e.g., threads may be substituted with press-fittings or welds). Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The invention claimed is:

1. A kit for implanting a nucleus replacement device, comprising:
 a spinal implant device comprising:
  an inner fillable enclosure having a proximal end with a proximal opening and a distal end with a distal opening;
  an outer fillable enclosure having a proximal end and a distal end, wherein the proximal ends of the inner and outer fillable enclosures are coupled together and the distal ends of the inner and outer fillable enclosures are coupled together so that the outer fillable enclosure encapsulates the inner fillable enclosure;
  a distal plug configured to seal the distal opening in the distal end of the inner fillable enclosure; and a proximal plug configured to seal the proximal opening in the proximal end of the inner fillable enclosure, the proximal plug having an access lumen for providing access to the inner fillable enclosure and a receptacle with an aperture for providing access to the outer fillable enclosure, wherein the access lumen for providing access to the inner fillable enclosure is configured to remain open after implantation; and an inflation stylus adapted to mate with the proximal plug, wherein the inflation stylus comprises:

an adjustable first lumen for movably extending through the access lumen to deliver and remove fluid from the inner fillable enclosure; and a second lumen for delivering fluid to the outer fillable enclosure.

2. The kit of claim 1, further comprising a reinforcing band surrounding a perimeter of the outer fillable enclosure.

3. The kit of claim 2, wherein the reinforcing band comprises a textile.

4. The kit of claim 2, further comprising a control element coupled to the reinforcing band.

5. The kit of claim 4, further comprising at least one pull string coupled to an edge of the reinforcing band.

6. The kit of claim 5, wherein the at least one pull string is sewn into a channel in the reinforcing band.

7. The kit of claim 5, further comprising a delivery sheath surrounding the inflation stylus, wherein the delivery sheath is movable from a delivery position to a deployed position.

8. The kit of claim 7, wherein the control element and at least one pull string are positioned between the delivery sheath and the inflation stylus.

9. The kit of claim 1, further comprising a curable silicone material for injection into the outer fillable enclosure.

10. The kit of claim 9, wherein the curable silicone material substantially cures within five minutes.

11. The kit of claim 1, further comprising a retaining element for retaining the device on the inflation stylus.

12. The kit of claim 1, wherein the distal plug defines a cylindrical recess for receiving a distal end of the inflation stylus.

13. The kit of claim 12, wherein the distal plug defines a second recess opposite the cylindrical recess for receiving the distal end of the inflation stylus.

14. The kit of claim 1, wherein the proximal plug is configured to have one or more features to assist in locating the proximal plug within a proximal neck of the inner fillable enclosure.

15. The kit of claim 1, wherein the access lumen is configured to prevent improper installation of the inflation stylus, and wherein the aperture is a skived hole.

16. The kit of claim 1, wherein exterior dimensions of the filled implant device are approximately 30 mm in length, 20 mm in width, and 10 mm in height.

17. The kit of claim 1, wherein exterior dimensions of the inner fillable enclosure are approximately 9 mm in length, 6 mm in width, and 6 mm thick.

18. The kit of claim 1, wherein the implant device is configured to expand at least 100% of its original size.

19. The kit of claim 1, wherein the inner fillable enclosure, the proximal plug, and the distal plug define an inner chamber, and wherein the proximal plug is made of silicone.

20. The kit of claim 19, wherein the access lumen is configured to vent the inner chamber.

* * * * *